(12) United States Patent
Saku et al.

(10) Patent No.: US 11,969,597 B2
(45) Date of Patent: Apr. 30, 2024

(54) BLOOD PRESSURE CONTROLLING APPARATUS, NON-TRANSITORY COMPUTER READABLE RECORDING MEDIUM STORING CONTROL PROGRAM OF BLOOD PRESSURE CONTROLLING APPARATUS, AND METHOD FOR CONTROLLING BLOOD PRESSURE

(71) Applicant: Kyushu University, National University Corporation, Fukuoka (JP)

(72) Inventors: Keita Saku, Fukuoka (JP); Kenji Sunagawa, Fukuoka (JP); Takeshi Tohyama, Fukuoka (JP); Kazuya Hosokawa, Fukuoka (JP); Takafumi Sakamoto, Fukuoka (JP)

(73) Assignee: Kyushu University, National University Corporation, Fukuoka (JP)

( * ) Notice: Subject to any disclaimer, the term of this patent is extended or adjusted under 35 U.S.C. 154(b) by 226 days.

(21) Appl. No.: 17/288,904

(22) PCT Filed: Nov. 1, 2019

(86) PCT No.: PCT/JP2019/044036
§ 371 (c)(1),
(2) Date: Apr. 26, 2021

(87) PCT Pub. No.: WO2020/091081
PCT Pub. Date: May 7, 2020

(65) Prior Publication Data
US 2021/0393963 A1    Dec. 23, 2021

Related U.S. Application Data
(60) Provisional application No. 62/753,931, filed on Nov. 1, 2018.

(51) Int. Cl.
*A61N 1/36*        (2006.01)
(52) U.S. Cl.
CPC ..... *A61N 1/36135* (2013.01); *A61N 1/36157* (2013.01); *A61N 1/36178* (2013.01); *A61N 1/36196* (2013.01)
(58) Field of Classification Search
CPC ........... A61N 1/36135; A61N 1/36157; A61N 1/36178; A61N 1/36196; A61N 1/36117; A61N 1/36139
See application file for complete search history.

(56) References Cited

U.S. PATENT DOCUMENTS

2002/0077563 A1* 6/2002 Sweeney ............. A61B 5/0031
                                                        600/510
2005/0149132 A1* 7/2005 Libbus ............... A61N 1/36139
                                                        607/9
(Continued)

FOREIGN PATENT DOCUMENTS

| CN | 1652841 A | 8/2005 |
| CN | 105455797 A | 4/2016 |

(Continued)

OTHER PUBLICATIONS

International Search Report dated Feb. 10, 2020 in connection with International Application No. PCT/JP2019/044036.
(Continued)

*Primary Examiner* — Amanda K Hulbert
(74) *Attorney, Agent, or Firm* — Wolf, Greenfield & Sacks, P.C.

(57) ABSTRACT

A blood pressure controlling apparatus includes an acquiring part configured to acquire biological information indicating blood pressure of a subject, a producing part configured to produce a frequency modulated pulse train on the basis of the biological information, and a supplying part configured to supply an electrical current on the basis of the frequency (Continued)

modulated pulse train, to an electrode attached on the subject. The electrical current stimulates baroreceptor afferent nerves of the subject.

19 Claims, 9 Drawing Sheets

(56) References Cited

U.S. PATENT DOCUMENTS

| | | | |
|---|---|---|---|
| 2007/0239210 A1 | 10/2007 | Libbus et al. | |
| 2015/0142082 A1 | 5/2015 | Simon et al. | |

FOREIGN PATENT DOCUMENTS

| | | | |
|---|---|---|---|
| JP | 2004-065529 A | 3/2004 | |
| JP | 2004-526471 A | 9/2004 | |
| JP | 2008-520376 A | 6/2008 | |
| JP | 2010-519960 A | 6/2010 | |
| JP | 2011-036697 A | 2/2011 | |
| JP | 2014-516297 A | 7/2014 | |

OTHER PUBLICATIONS

Extended European Search Report dated Jun. 24, 2022 in connection with European Application No. 19879295.4.

Hosokawa et al., Closed-loop neuromodulation technology for baroreflex blood pressure control. Proceedings of the IEEE. Feb. 2016;104(2):432-43. DOI: 10.1109/JPROC.2015.2496290.

Tohyama et al., Smart baroreceptor activation therapy strikingly attenuates blood pressure variability in hypertensive rats with impaired baroreceptor. Hypertension. Mar. 2020;75(3):885-92. DOI: 10.1161/HYPERTENSIONAHA.119.13673 URL:https://www.ahajournals.org/doi/pdf/10.1161/HYPERTENSIONAHA.119.13673.

Japanese Office Action dated Jun. 6, 2023 in connection with Japanese Application No. 2021-523330.

Japanese Notice of Allowance dated Nov. 21, 2023 in connection with Japanese Application No. 2021-523330.

PCT/JP2019/044036, Feb. 10, 2020, International Search Report.

Chinese Office Action dated Dec. 23, 2023, in connection with for Chinese Application No. 201980070863.7.

\* cited by examiner

BLOOD PRESSURE CONTROLLING APPARATUS, NON-TRANSITORY COMPUTER READABLE RECORDING MEDIUM STORING CONTROL PROGRAM OF BLOOD PRESSURE CONTROLLING APPARATUS, AND METHOD FOR CONTROLLING BLOOD PRESSURE

CROSS-REFERENCE TO RELATED APPLICATIONS

This application is a 35 U.S.C. § 371 National Phase filing of International Application No. PCT/JP2019/044036, filed on Nov. 1, 2019, entitled "BLOOD PRESSURE CONTROLLING APPARATUS, NON-TRANSITORY COMPUTER READABLE RECORDING MEDIUM STORING CONTROL PROGRAM OF BLOOD PRESSURE CONTROLLING APPARATUS, AND METHOD FOR CONTROLLING BLOOD PRESSURE," which claims priority to and the benefit of U.S. Provisional Patent Application No. 62/753,931, filed on Nov. 1, 2018. The entire contents of these applications are incorporated herein by reference in their entirety.

TECHNICAL FIELD

The present disclosure relates to a blood pressure controlling apparatus, a non-transitory computer readable recording medium storing a control program of the blood pressure controlling apparatus, and a method for controlling blood pressure.

In particular, the present disclosure relates to systems and methods for autonomic closed-loop neuromodulation in regulating mean blood pressure (BP) and BP variability to treat patients with hypertension, pressure dysregulation and/or heart failure. The system operates in parallel with the native baroreflex system, augments the baroreflex regulation of BP and makes it possible to quantitatively programmable control of both mean BP and BP variability.

Priority is claimed on U.S. Provisional Patent Application No. 62/753,931, filed Nov. 1, 2018, the content of which is incorporated herein by reference.

BACKGROUND ART

Cardiovascular disease remains the leading cause of death worldwide. Among various cardiovascular pathophysiologies, hypertension is by far the most prevalent (more than 50% of general population >60 years, one billion patients globally). Despite marked progress in medical treatment of hypertension, nearly 10% of patients are treatment resistant (3 drugs or more, BP>140/90 mmHg). Furthermore, recent clinical trials revealed that the long-term cardiovascular events not only depend on the BP level but also depend on BP variability. Although most antihypertensive agents are capable of lowering mean BP, no antihypertensive agents ever successfully lowered BP variability. This is a huge global healthcare issue, because of massive prevalence of hypertension, and mandates urgent solutions. To overcome the limitations of drug treatment of hypertension, we developed an autonomic closed-loop neuromodulation system in programmatically regulating mean BP and BP variability.

Circulatory homeostasis is the essential infrastructure to support our normal physiology and life. For this purpose, nature developed complex neuro-hormonal regulatory systems in the cardiovascular system. Among the regulatory systems, the autonomic nervous system plays the central role in regulating and stabilizing BP. Physiological studies indicated that BP induced stretching of the baroreceptors in the arterial wall activates the baroreceptor afferent nerves, suppresses sympathetic nerve activity via the vasomotor center in the brainstem, and reduces BP. Since the baroreceptors sense the reduced BP, the baroreceptor induced blood pressure regulation configures a negative feedback system (baroreflex system).

In the related art, a blood pressure control apparatus is known (for example, see Patent Document 1). This blood pressure control apparatus has a blood pressure sensor as a blood pressure detecting means for detecting a blood pressure value of a living body and an electric stimulation part outputting stimulative electricity to be given to the spinal sympathetic nervous system of the living body. The electric stimulation part comprises a stimulation frequency control part which calculates the stimulation frequency of a stimulative electricity that needs to be given to the spinal sympathetic nervous system of the living body for raising the blood pressure value of the living body to a target set value, and a pulse current output part which outputs the stimulative electricity of the stimulation frequency calculated by the control part.

CITATION LIST

Patent Literature

[Patent Document 1]
Japanese Unexamined Patent Application, First Publication No. 2004-065529

SUMMARY OF INVENTION

Technical Problem

The device based activation of baroreflex has been explored many years ago. However, technological immaturity prevented us from applying neuromodulation therapy for the treatment of hypertension as a therapeutic option. Recently, the baroreflex activation therapy has been revisited, and has shown the significant impact in lowering BP. However, the device continuously stimulated the baroreceptors or baroreceptor afferent nerves at a constant rate without BP feedback. This means that neuromodulators have no way of knowing how strongly or weakly they need to stimulate the baroreceptor afferent nerves in the presence of widely varying physiological drive of the autonomic nervous system. To overcome this limitation of baroreflex activation therapy, the present inventors previously developed a baroreflex activation therapy with a closed-feedback loop. This system allows us to restore normal baroreflex function in the absence of native baroreflex system. However, it was still not possible to make mean BP and BP variability fully programmable.

Solution to Problem

In the present system, the present inventors augment the native baroreflex system by having an additional neuromodulation system with closed-feedback in parallel with the native baroreflex system and configure the system to make mean BP and BP variability fully programmable.

An object of the present disclosure is to provide a blood pressure controlling apparatus, a non-transitory computer readable recording medium storing a control program of the blood pressure controlling apparatus, and a method for controlling blood pressure, capable of independently controlling a mean of the blood pressure and variability of the blood pressure, and capable of improving volume tolerance and resolving pulmonary congestion in acute heart failure.

According to the present disclosure, there is provided a blood pressure controlling apparatus comprising an acquiring part configured to acquire biological information indicating blood pressure of a subject, a producing part configured to produce a frequency modulated pulse train on the basis of the biological information, and a supplying part configured to supply an electrical current on the basis of the frequency modulated pulse train, to an electrode attached on the subject, wherein the electrical current stimulates baroreceptor afferent nerves of the subject.

According to the present disclosure, there is provided a non-transitory computer readable recording medium storing a control program of a blood pressure controlling apparatus, the control program making the blood pressure controlling apparatus perform at least acquiring biological information indicating blood pressure of a subject, producing a frequency modulated pulse train on the basis of the biological information, and supplying an electrical current on the basis of the frequency modulated pulse train, to an electrode attached on the subject, wherein the electrical current stimulates baroreceptor afferent nerves of the subject.

According to the present disclosure, there is provided a method for controlling blood pressure, the method comprising acquiring biological information indicating blood pressure of a subject, producing a frequency modulated pulse train on the basis of the biological information, and supplying an electrical current on the basis of the frequency modulated pulse train, to an electrode attached on the subject, wherein the electrical current stimulates baroreceptor afferent nerves of the subject.

Cardiovascular disease remains the leading cause of death worldwide. Among cardiovascular pathophysiologies, hypertension is by far the most prevalent disease leading to stroke, ischemic heart disease, heart failure and death. Although many effective antihypertensive agents have been developed, nearly 10% of treated patients are treatment resistant. Furthermore, recent studies indicated not only mean BP but also BP variability are equally important in determining the long-term outcome of hypertension patients. It is well established that most antihypertensive agents are capable of lowering mean BP. It is unfortunate; however, no antihypertensive agents ever successfully lowered BP variability. This is a huge global healthcare issue, because of massive prevalence of hypertension, thereby inevitably mandates urgent solutions. The present disclosure relates to systems and methods for autonomic closed-loop neuromodulation in regulating mean blood pressure (BP) and BP variability to treat patients with hypertension, pressure dysregulation and/or heart failure. The system operates in parallel with the native baroreflex system, augments the baroreflex regulation of BP and makes both mean BP and BP variability fully programmable.

Advantageous Effects of Invention

According to the present disclosure, it is possible to provide a blood pressure controlling apparatus, a non-transitory computer readable recording medium storing a control program of the blood pressure controlling apparatus, and a method for controlling blood pressure, capable of independently controlling a mean of the blood pressure and variability of the blood pressure, and capable of improving volume tolerance and resolving pulmonary congestion in acute heart failure.

Acute heart failure (AHF) increases sympathetic nerve activity (SNA) which, in turn, increases pre- and after-load and frequently leads to hypertension with life threatening pulmonary edema. Thus, sympathetic unloading is a reasonable therapeutic option. In addition, the baroreflex failure deteriorates volume tolerance, and increases the risk of pulmonary congestion. Since sBAT (smart baroreflex activation therapy) reduces SNA with keeping hemodynamics, sBAT markedly improves volume tolerance and instantly (within 5 seconds) resolves pulmonary congestion in AHF model rats.

DESCRIPTION OF EMBODIMENTS

First Embodiment

Hereinafter, embodiments of the present disclosure will be described with reference to the drawings. First, a configuration of a system to which a blood pressure controlling apparatus according to a first embodiment will be described with reference to FIG. 1.

Figure 1:
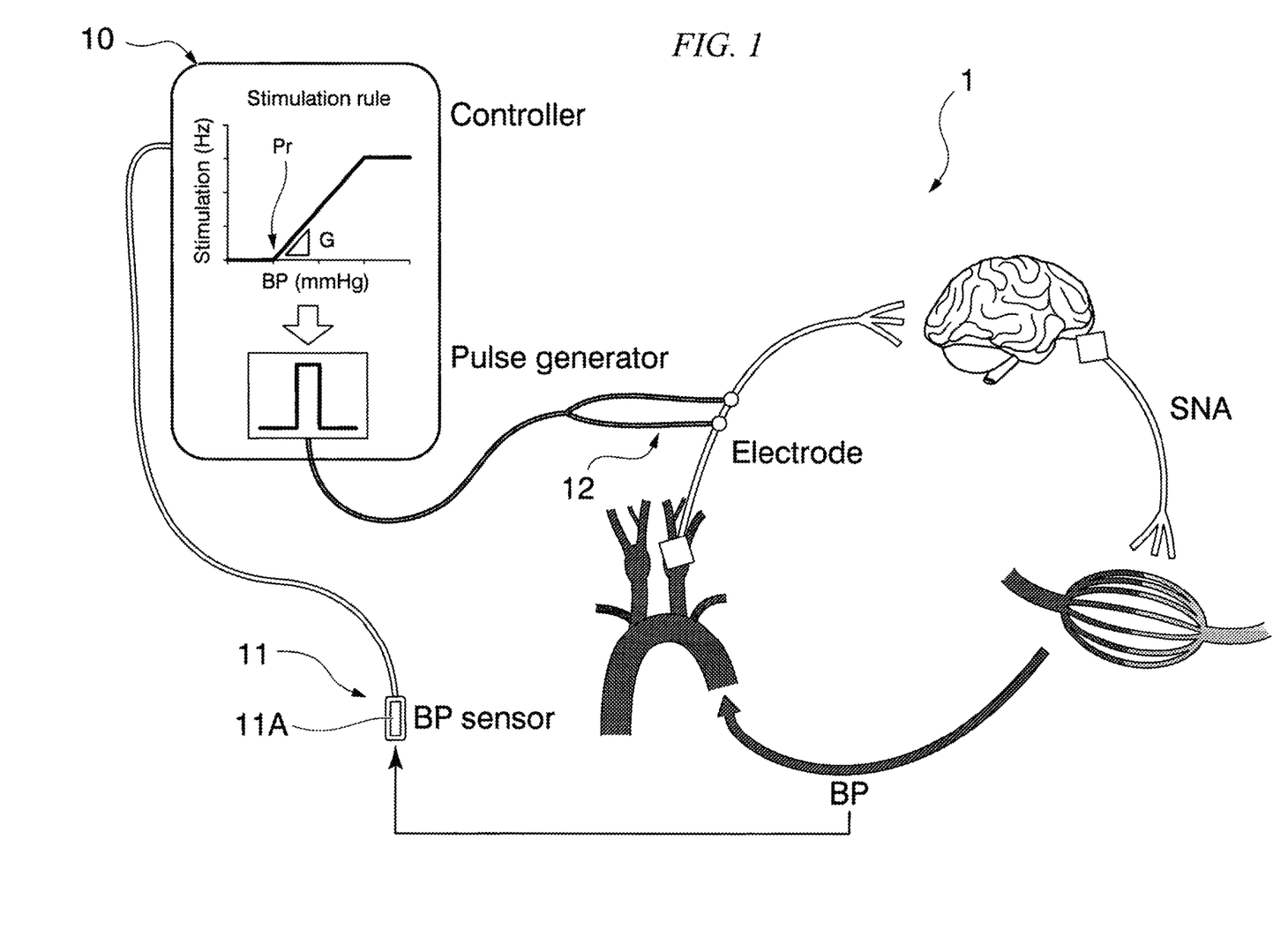
FIG. 1 is a schematic illustration of the entire system.

FIG. 1 is a schematic illustration of an autonomic closed-loop neuromodulation system 1. The system 1 consists of 4 major components, a blood pressure sensing component, a controller component to encode blood pressure (BP) to frequency modulated pulse trains, and a neurostimulator component to stimulate the baroreceptor afferent nerves and a nerve electrode component to drive the stimulation current to activate the baroreceptor afferent nerves.

In an example shown in FIG. 1, the blood pressure sensing component functions as a detecting part 11. The detecting part 11 includes a blood pressure sensor 11A. The blood pressure sensor detects the blood pressure of a subject. The blood pressure detected by the blood pressure sensor functions as biological information.

In another example, the detecting part 11 may include another sensor (not shown) which detects blood pressure surrogate variables such as vascular strain, instantaneous flow and/or pulse wave velocity. The blood pressure surrogate variables function as the biological information.

In the example shown in FIG. 1, the controller component and the neurostimulator component function as a blood pressure controlling apparatus 10.

Figure 2:
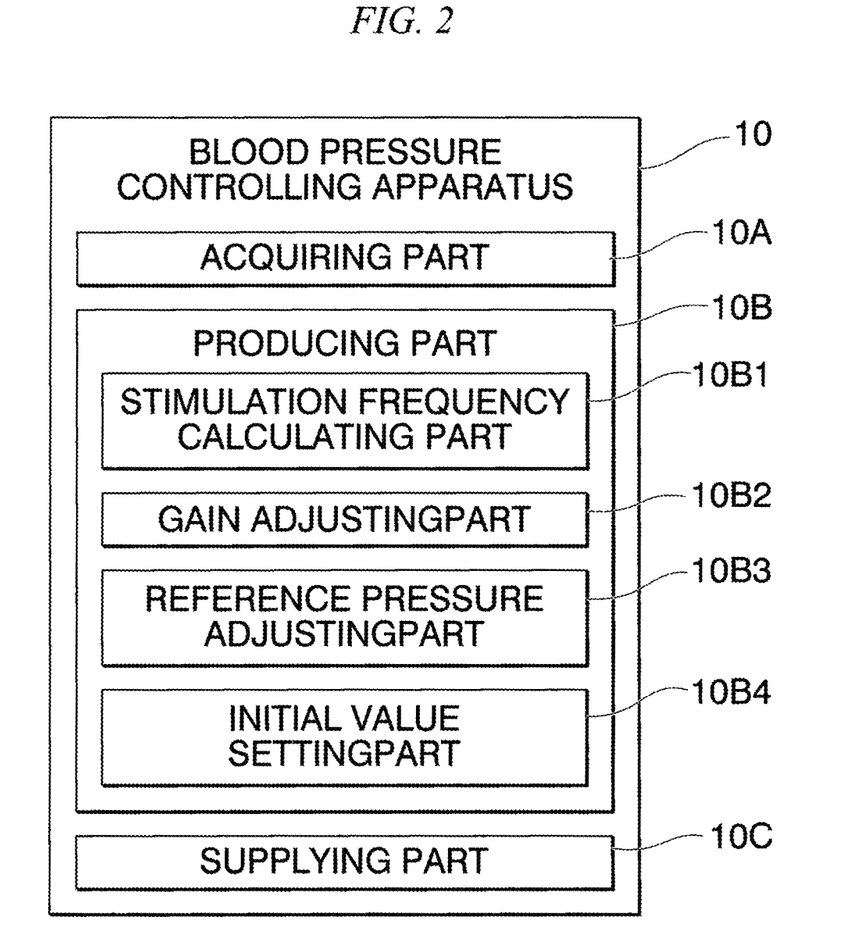
FIG. 2 shows a schematic illustration of a blood pressure controlling apparatus.

FIG. 2 shows a schematic illustration of the blood pressure controlling apparatus 10. The blood pressure controlling apparatus 10 includes acquiring part 10A, producing part 10B and supplying part 10C. The acquiring part 10A acquires the biological information indicating the blood pressure detected by the blood pressure sensor 11A. The producing part 10B produces a frequency modulated pulse train on the basis of the biological information acquired by the acquiring part 10A.

The producing part 10B includes stimulation frequency calculating part 10B1, gain adjusting part 10B2, reference pressure adjusting part 10B3, and initial value setting part 10B4. The stimulation frequency calculating part 10B1 calculates a stimulation frequency of the frequency modulated pulse train on the basis of a gain, reference pressure, and the blood pressure indicated by the biological information. Particularly, the stimulation frequency calculating part 10B1 calculates the stimulation frequency by multiplying a difference between the reference pressure and the blood pressure by the gain.

The gain adjusting part 10B2 adjusts a value of the gain. The reference pressure adjusting part 10B3 adjusts a value of the reference pressure. The initial value setting part 10B4 sets an initial value of the gain and an initial value of the reference pressure.

The supplying part 10C supplies an electrical current on the basis of the frequency modulated pulse train produced by the producing part 10B, to an electrode 12 (see FIG. 1) attached on the subject. The electrical current stimulates the baroreceptor afferent nerves of the subject.

Since the stimulation of baroreceptor afferent nerves lowers the BP, the system 1 configures a closed-loop negative feedback system which operates in parallel with a native baroreflex system. Because of the parallel configuration of the system 1, the system makes mean BP (mean of the blood pressure) and BP variability (variability of the blood pressure) programmable.

Figure 3:
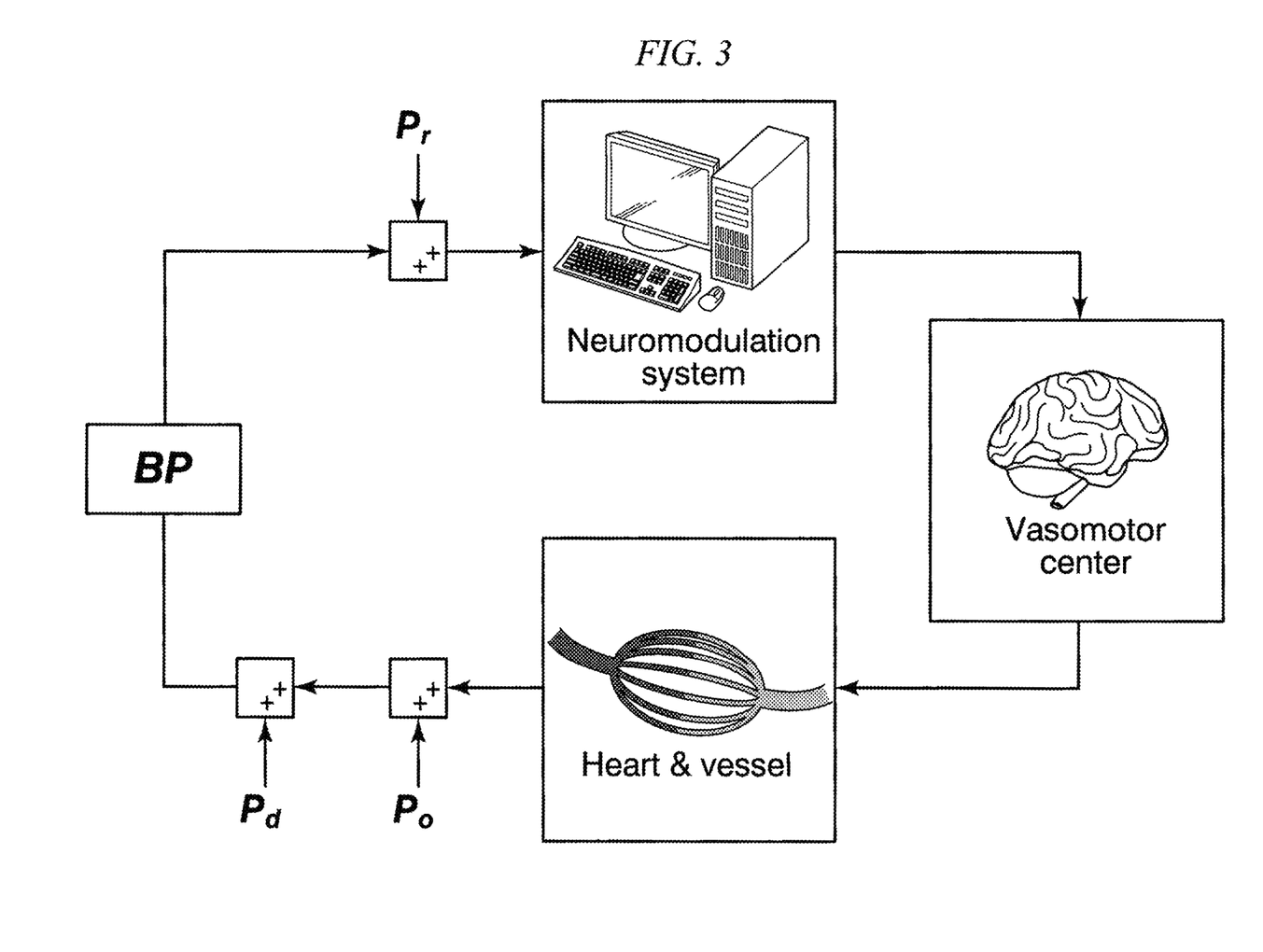
FIG. 3 shows a functional block diagram of the system to explain the theory of operation.

FIG. 3 is a functional block diagram of the system 1 to illustrate the theory of operation. From the diagram, the operating BP can be derived by Expression (1) below.

[Math. 1]

$$BP = \frac{G}{1+G}P_r + \frac{1}{1+G}P_o + \frac{1}{1+G}P_d \qquad (1)$$

In Expression (1), 4 parameters are the gain G, the reference pressure $P_r$, baseline pressure $P_o$ and pressure disturbance $P_d$. The first two terms of Expression (1) indicate the mean BP independent of the pressure disturbance $P_d$ which becomes as following Expression (2).

[Math. 2]

$$P_m = \frac{G}{1+G}P_r + \frac{1}{1+G}P_o = P_r + \frac{1}{1+G}(P_o - P_r) \qquad (2)$$

In Expression (2), $P_m$ is the mean BP. Expression (2) indicates that the mean BP $P_m$ is predominantly determined by the reference pressure $P_r$. For the realistic values of the baseline pressure $P_o$ and the reference pressure $P_r$ such as $P_o=140$ and $P_r=100$ mmHg, for the realistic changes in the gain G from 0.5 to 2, the mean BP $P_m$ changes only by 10 mmHg as long as the reference pressure $P_r$ remains unchanged.

The last term of Expression (1) indicates that increases in the gain G attenuate hyperbolically the impact of the pressure disturbance Pa on the BP. For the gain G=1 the impact of the pressure disturbance $P_d$ on the BP reduces to ½ of its original magnitude.

With this system configuration, by adjusting the reference pressure $P_r$ and the gain G, the control of both the mean BP and the BP variability can be made programmable.

Figure 4:
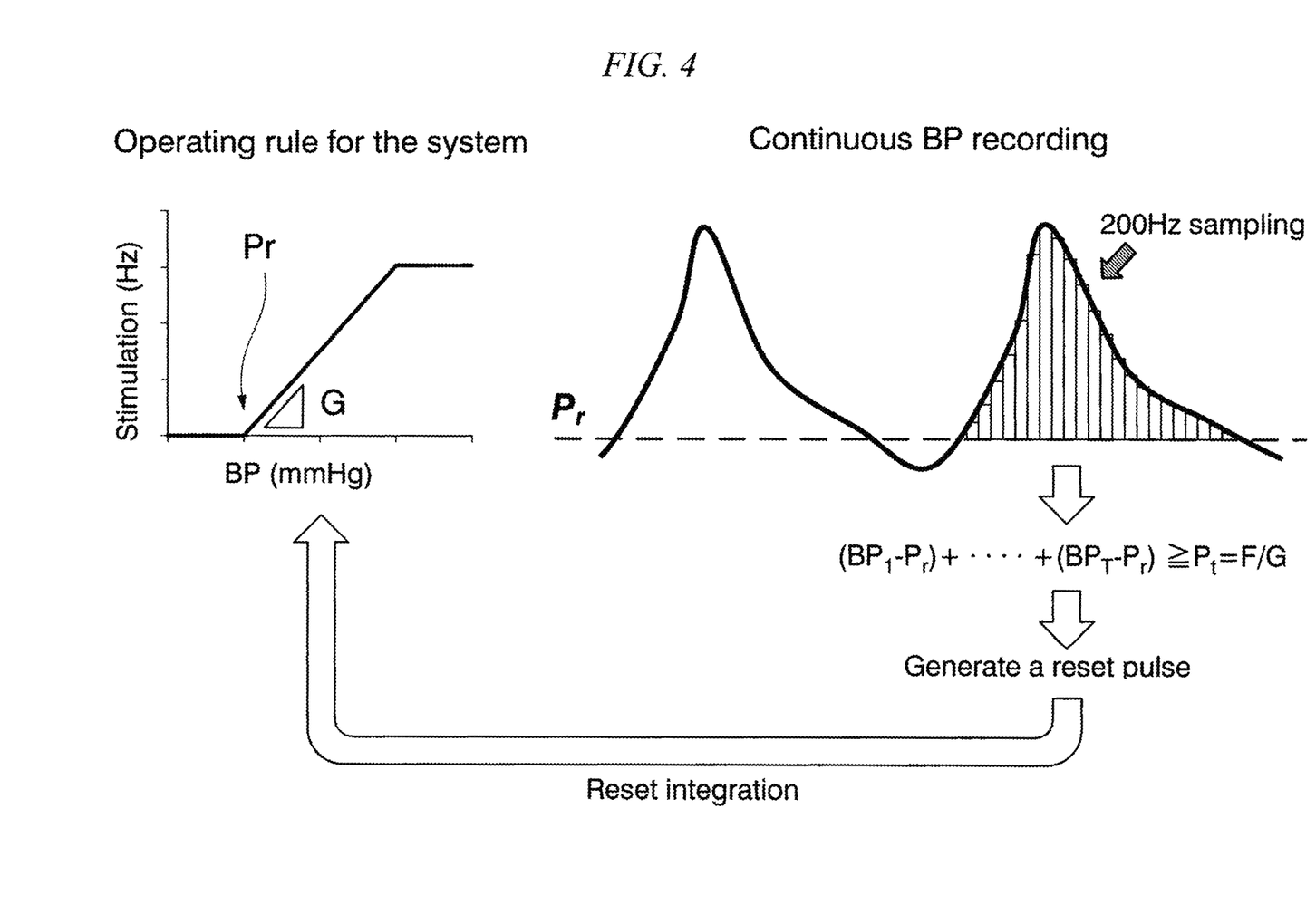
FIG. 4 shows how measured BP is encoded as frequency modulated pulse trains to stimulate baroreceptor afferent nerves to establish closed-feedback neuromodulation.

FIG. 4 illustrates how, in the controller, measured BP is encoded as frequency modulated pulse trains to stimulate baroreceptor afferent nerves and establish the closed-feedback neuromodulation with the feature of programmable mean BP and BP variability. In the research of the present inventors, a resettable integrator was used with a prespecified threshold for the conversion of the BP to frequency modulated pulse trains. Digitized BP at a sampling rate of 200 Hz in excess of the reference pressure $P_r$ is instantaneously integrated until the integral reaches the prespecified threshold $P_t$. Once it reaches the threshold $P_t$, the controller generates a pulse, resets the integrator and starts new integration. Thus, the time T required to reach the reference pressure $P_r$ becomes shorter for large BP and longer for small BP, and, a reset pulse frequency (1/T) is proportional to the BP. By this direct frequency modulation mechanism, this encoder generates frequency modulated pulse trains proportional to the BP. The gain G can be easily changed by changing the prespecified threshold $P_t$. This algorithm simplifies its realization and implementation because it is based on the BP integration, thereby immune to contaminated noises in the BP. Needless to say, this controller can be realized physically as well as logically.

As mentioned above, the stimulation frequency calculating part 10B1 (see FIG. 2) calculates the stimulation frequency by multiplying the difference between the reference pressure $P_r$ and the BP detected by the blood pressure sensor 11A (see FIG. 1), by the gain G The gain adjusting part 10B2 (see FIG. 2) adjusts the value of the gain G between 0.5 and 3, for example. The reference pressure adjusting part 10B3 (see FIG. 2) adjusts the value of the reference pressure $P_r$ between 40 mmHg and 80 mmHg, for example. Namely, as the BP detected by the blood pressure sensor 11A becomes larger than the reference pressure $P_r$, the stimulation frequency increases. On the other hand, in Patent Document 1, as the blood pressure detected by the blood pressure sensor becomes smaller than a predetermined reference pressure such as 100 mmHg, the stimulation frequency increases.

In the blood pressure controlling apparatus 10 according to the first embodiment, the gain adjusting part 10B2 adjusts the value of the gain G on the basis of the variability of the blood pressure indicated by the biological information. Particularly, the gain adjusting part 10B2 increases the value of the gain G when the variability of the blood pressure is larger than a predetermined value. Accordingly, in the blood pressure controlling apparatus 10 according to the first embodiment, the variability of the blood pressure can be controlled appropriately.

The quantitative relationship between the BP, the gain G and the threshold $P_t$ are as follows: Based on previous studies of the present inventors, a stimulation pulse was used with the duration of 0.2 msec. The linear slope of the stimulation frequency F and BP drop $BP_{out}$ relation due to baroreflex gives the stimulation frequency to BP drop conversion factor $C_{fp}$ as Expression (3) below.

[Math. 3]

$$BP_{out} = C_{fp}F \qquad (3)$$

Based on the previous studies of the present inventors, the amplitude of the stimulation pulse in volts is determined to attain the BP drop of 30 mmHg at the stimulation frequency of 10 Hz. This gives the BP drop conversion factor $C_{fp}$ as Expression (4) below.

[Math. 4]

$$C_{fp}=30/10=3 \text{ mmHg/Hz} \tag{4}$$

The present inventors define the conversion factor $C_{pf}$ from the BP to neurostimulation frequency, which linearly relates the stimulation frequency F in response to BP ($BP_{in}$) to represent baroreceptor transduction as Expression (5) below.

[Math. 5]

$$F=C_{pf}BP_{in} \text{ Hz} \tag{5}$$

Substituting F in Expression (3) with Expression (5) gives Expression (6) below.

[Math. 6]

$$BP_{out}=C_{fp}C_{pf}BP_{in} \text{ mmHg} \tag{6}$$

Thus the baroreflex total loop gain G is given by Expression (7) below.

[Math. 7]

$$G=C_{fp}C_{pf} \text{ mmHg/mmHg} \tag{7}$$

Therefore, the present inventors can adjust the gain G for a given BP drop conversion factor $C_{fp}=3$ by changing the conversion factor $C_{pf}$ as Expression (8) below.

[Math. 8]

$$G=3C_{pf} \text{ mmHg/mmHg} \tag{8}$$

The present inventors exemplify how to define the total loop gain G, and thereby the conversion factor $C_{pf}$ by using the algorithm to convert the BP to the stimulation frequency as explained above. The time T required to reach the prespecified threshold $P_t$ (mmHg·sec), depends on two factors, the BP and the prespecified threshold $P_t$. For the sake of simplicity, suppose that the BP is constant during integration. Then the time T becomes as Expression (9) below.

[Math. 9]

$$T=P_t/BP \text{ sec} \tag{9}$$

Since the stimulation frequency F is the reciprocal of the time T, the stimulation frequency F is given as Expression (10) below.

[Math. 10]

$$F=1/T=BP/P_t \text{ Hz} \tag{10}$$

Thus, the stimulation frequency F is proportional to the BP. The conversion factor $C_{pf}$ becomes as Expression (11) below.

[Math. 11]

$$C_{pf}=1/P_t \text{ Hz/mmHg} \tag{11}$$

Substituting the conversion factor $C_{pf}$ in Expression (8) with Expression (11) yields Expression (12) below.

[Math. 12]

$$G=3/P_t \text{ mmHg/mmHg} \tag{12}$$

Therefore, the gain G can be adjusted to desired values by adjusting the prespecified threshold $P_t$.

The generality of this formulation holds even if the BP changes during integration. In this case, the time T becomes the time required the integral of the BP to reach the prespecified threshold $P_t$.

In experiment of the present inventors, the value of the gain G ranges from 0.5 to 3 which corresponds to the value of the prespecified threshold $P_t$ from 1 to 6.

In Expression (7), the gain G is a product of the conversion factor $C_{pf}$ and the BP drop conversion factor $C_{fp}$. In the real physiological system, the BP drop conversion factor $C_{fp}$ is physiologically frequency dependent which makes the gain G also frequency dependent as Expression (13) below.

[Math. 13]

$$G(f)=C_{pf}C_{fp}(f) \tag{13}$$

In Expression (13), the conversion factor $C_{pf}$ is a non-frequency dependent scaler. As explained above, the conversion factor $C_{pf}$ is changed to the gain G. Since the conversion factor $C_{pf}$ is a scaler, it does not affect the frequency characteristics of the gain G(f). The conversion factor $C_{pf}$ is also made frequency dependent as Expression (14) below.

[Math. 14]

$$G(f)=C_{pf}(f)C_{fp}(f) \tag{14}$$

Expression (14) indicates that the frequency characteristics of the baroreflex total loop G(f) can be modulated by changing the conversion factor $C_{pf}(f)$. This implies that the BP variability can be suppressed in the conversion factor $C_{pf}(f)$ defined selective frequencies. For instance, if the conversion factor $C_{pf}(f)$ is programmed so that the corner frequency of the total baroreflex loop becomes 0.05 Hz (2 times of normal), its impact on the BP manifests as a quick recovery from pressure disturbance such as orthostatic pressure fall. This is to say that the mean BP is suppressed but the pressure recover from orthostatic stress is accelerated. Such a programmable dynamic response is a very unique feature of the system that can never be achieved by any anti-hypertensive agents.

System can operate an alternative algorithm of frequency modulated pulse train generation. This uses a voltage controlled oscillator. Previous physiological studies indicated that the dominant corner frequency of baroreflex pressure regulation ranges 0.01-0.03 Hz in various animal species (rat, cat, rabbit and dog). Since the corner frequencies are relatively constant across various animal species, the present inventors assumed the dominant corner frequency of human also resides in this frequency range. If this is the case, unlike the first algorithm in which rapid direct frequency modulated pulse trains proportional BP is generated, the frequency modulation encoder does not necessarily update the pulse frequency instantaneously. The present inventors low-pass filtered instantaneous BP and decimated it at 1.0 Hz. The decimated BP drives the voltage controlled oscillator and generates frequency modulated pulse trains proportional to BP. The oscillation frequency is updated every second.

How the present inventors adjust the reference pressure $P_r$ and the gain G to control the mean BP and the BP variability are as follows. Suppose that the BP without neuromodulation, i.e., baseline BP, is the baseline pressure $P_o$. The present inventors want to reduce the mean BP to a prespecified BP level $P_m$. The present inventors also want to reduce the BP variability to $1/\alpha$ of the pressure disturbance $P_d$.

From the last term of Expression (1), the gain G has to be adjusted to as Expression (1) below.

[Math. 15]

$$G = \alpha - 1 \qquad (15)$$

Once the gain G is adjusted, the reference pressure $P_r$ required to reduce the baseline pressure $P_o$ to the desired value of the BP, the mean BP $P_m$ can be estimated by rearranging Expression (2) as Expression (16) below.

[Math. 16]

$$P_r = P_m + \frac{1}{G}(P_m - P_o) \qquad (16)$$

An example of embodiments determining the gain G and the reference pressure $P_r$ is given. Suppose that the present inventors want to reduce the BP variability to ½ of the pressure disturbance $P_d$. From Expression (15), the present inventors find the gain G=1 for α=2. If the uncontrolled BP, the baseline pressure $P_o$ is 140 mmHg, and a prespecified operational BP, the mean BP $P_m$ is 100 mmHg, substituting those values into Expression (16) immediately yields the reference pressure $P_r$=60 mmHg. The present inventors have confirmed that this algorithm which independently controls the mean BP and the BP variability works in animal experiments.

The programmability of the mean BP $P_m$ by changing the reference pressure $P_r$ gives extraordinary freedom for the device to control the BP. Increasing in the gain G reduces the BP variability for sure. However, if the present inventors want to generate a physiological circadian pressure change in patients who lost such a function, the present inventors can generate this rhythm by programming the reference pressure $P_r$ to have a desired circadian rhythm. The potential of generating new BP rhythms is a very unique aspect of this invention.

In this application, the present inventors used an intra-arterial pressure sensor to know instantaneous arterial pressure. However, any pressure sensing mechanisms and its surrogates such as arterial strain estimated by various methods, pulse wave velocity, and arterial flow can be used.

As mentioned above, in the blood pressure controlling apparatus 10 according to the first embodiment, the producing part 10B produces the frequency modulated pulse train on the basis of the closed-loop negative feedback system which operates in parallel with the native baroreflex system to augment a native baroreflex function.

Also, in the blood pressure controlling apparatus 10 according to the first embodiment, the producing part 10B produces the frequency modulated pulse train on the basis of the biological information to control the mean BP and to attenuate the BP variability, independently.

In particular, in the blood pressure controlling apparatus 10 according to the first embodiment, the initial value setting part 10B4 sets the initial value of the reference pressure on the basis of therapeutic requirements or physiological blood pressure change in the subject.

In an example to which the blood pressure controlling apparatus 10 according to the first embodiment is applied, the producing part 10B produces the frequency modulated pulse train on the basis of instantaneous blood pressure indicated by the biological information. Particularly, the producing part 10B produces the frequency modulated pulse train on the basis of the instantaneous blood pressure indicated by the biological information by making use of limited baroreflex speed of physiological systems.

In an example to which the blood pressure controlling apparatus 10 according to the first embodiment is applied, the gain G adjusted by the gain adjusting part 10B2 is physiologically frequency dependent. Particularly, the gain G adjusted by the gain adjusting part 10B2 is frequency dependent to suppress the blood pressure and variability of the blood pressure frequency dependently.

In an example to which the blood pressure controlling apparatus 10 according to the first embodiment is applied, the gain G is calibrated according to the subject. Particularly, the initial value of the gain G set by the initial value setting part 10B4 is calibrated according to the subject.

As mentioned above, in the blood pressure controlling apparatus 10 according to the first embodiment, the gain adjusting part 10B2 adjusts the value of the gain G Particularly, the gain G is quantitatively adjusted to make the mean BP and the BP variability programmable. Namely, the blood pressure controlling apparatus 10 according to the first embodiment is applied to the system 1 (see FIG. 1) for independently controlling the mean BP and the BP variability.

Figure 5:
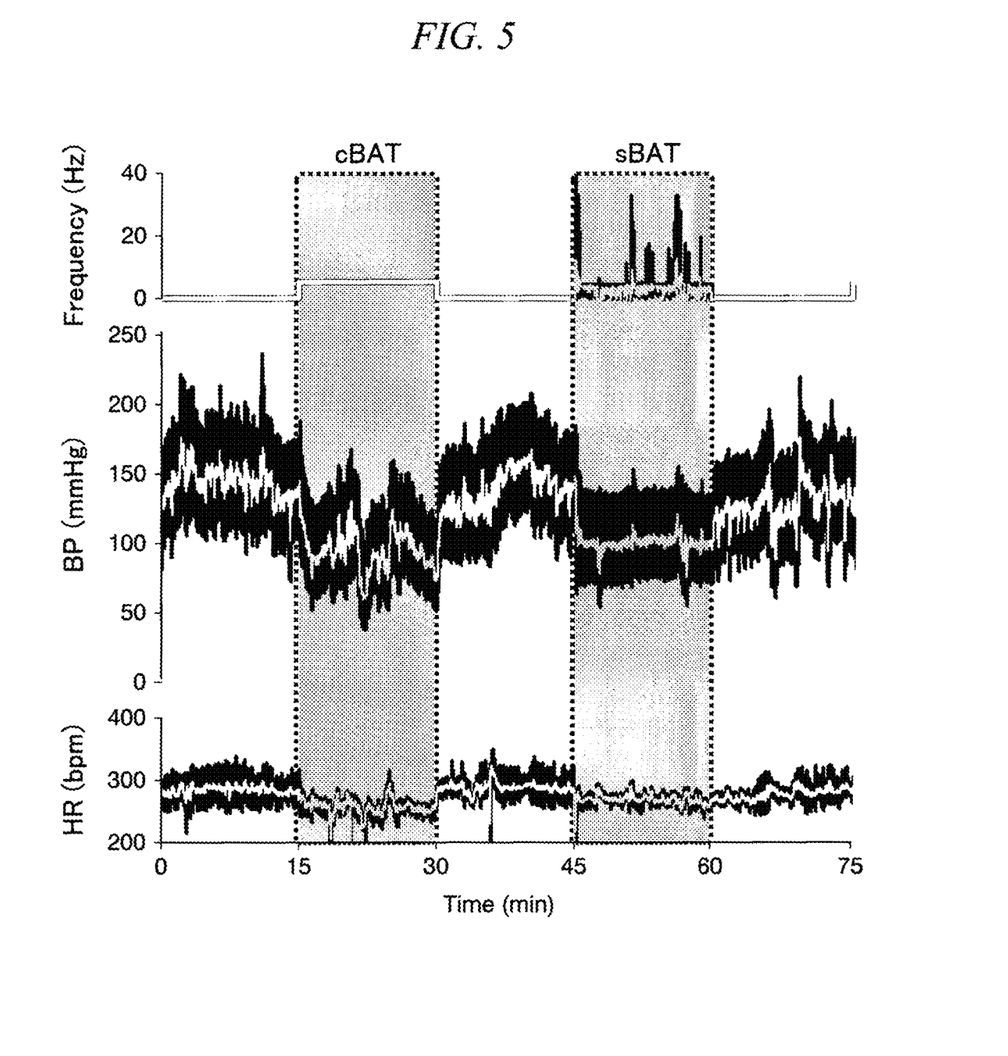
FIG. 5 shows performance of system operation in conscious rats.

FIG. 5 shows performance of system operation in conscious rats. In FIG. 5, cBAT shows baroreflex activation therapy with a continuous stimulation, and sBAT shows baroreflex activation therapy with closed-loop regulation of stimulation. As can be seen, the developed closed loop baroreceptor neuromodulation system (sBAT) markedly reduces the mean BP and the BP variability. In contrast, open-loop baroreceptor nerves stimulation at a constant frequency (average frequency of sBAT) (constant frequency stimulation, cBAT) can lower the BP but cannot attenuate the BP variability.

Figure 6:
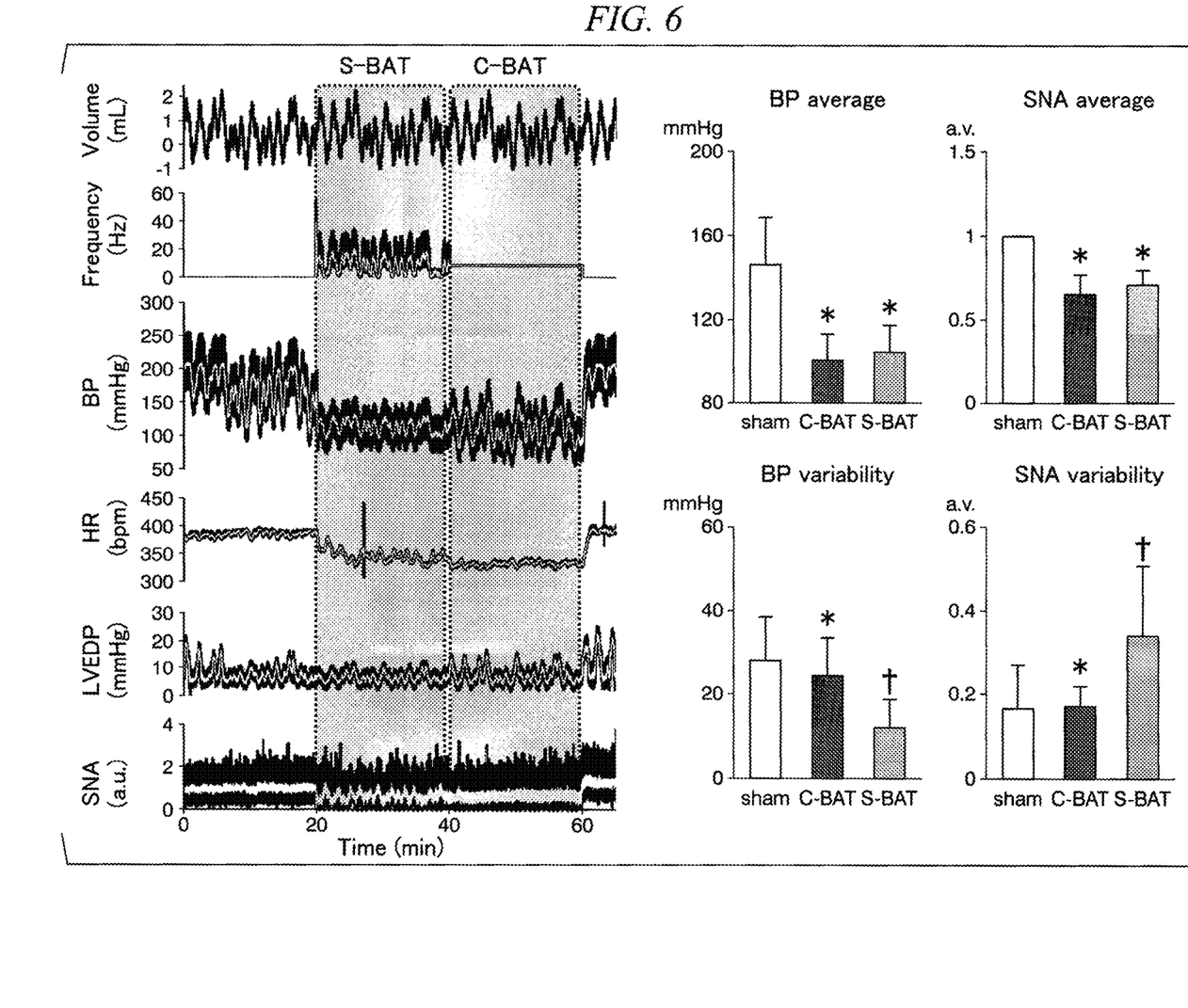
FIG. 6 shows results of experiment under volume perturbations in an anesthetized rat.

FIG. 6 shows results of experiment under volume perturbations in an anesthetized rat. In FIG. 6, HR shows heart rate, LVEDP shows left ventricular end-diastolic volume, and SNA shows sympathetic nerve activity. As shown in FIG. 6, the developed system (sBAT) markedly reduces the BP and the BP variability. In contrast, cBAT cannot attenuate the BP variability. Both sBAT and cBAT suppressed averaged SNA. However SNA variability is much larger in sBAT than in cBAT indicating that SNA is counter balancing exogenous changes in BP.

Second Embodiment

The blood pressure controlling apparatus 10 according to a second embodiment will be described. The blood pressure controlling apparatus 10 according to the second embodiment has the same configuration as the blood pressure controlling apparatus 10 according to the first embodiment except for points to be described below. Accordingly, in the blood pressure controlling apparatus 10 according to the second embodiment, it is possible to obtain the same advantageous effects as those of the blood pressure controlling apparatus 10 according to the first embodiment except for the points to be described below.

As mentioned above, the blood pressure controlling apparatus 10 according to the first embodiment is applied to the system 1 (see FIG. 1) for independently controlling the mean BP and the BP variability. The blood pressure controlling apparatus 10 according to the second embodiment is applied to a system for improving volume tolerance and resolving pulmonary congestion in acute heart failure.

AHF excessively activates SNA, markedly increases stressed volume and thereby left ventricular end-diastolic pressure (LVEDP), and often leads to hypertension and pulmonary edema. Therefore, sympathoinhibitory intervention is a reasonable, therapeutic option to this pathophysiology. However, such an intervention without causing intractable hypotension remains unestablished. The present inventors have developed a closed-loop neuromodulator which stimulates the carotid sinus (baroreceptor) nerves in response to changes in arterial pressure (AP) (sBAT). sBAT translates AP into stimulation and controls AP to desired levels via changing SNA.

The present inventors examined if sBAT suppresses LVEDP without inducing intractable hypotension in a rat model of AHF.

Figure 7:
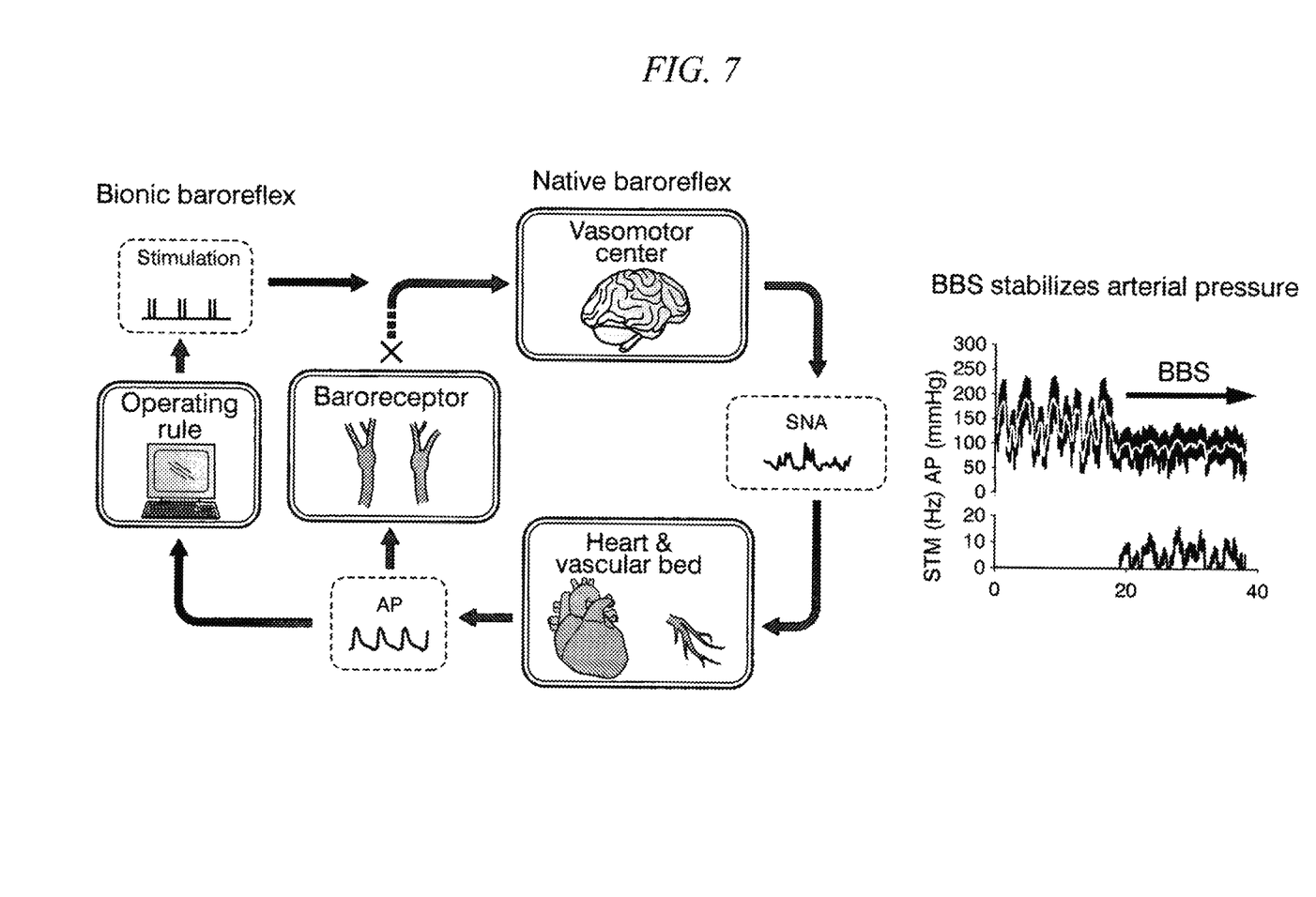
FIG. 7 shows a configuration of sBAT.

In 6 Sprague-Dawley rats, the present inventors created AHF by ligating coronary artery. The present inventors attached electrodes to bilateral carotid bifurcation. sBAT consists of a pressure sensor, a regulator, and a neurostimulator (see FIG. 7). In volume tolerance study, the present inventors infused donated blood (0 to 10 ml/kg) stepwise and observed changes in AP and LVEDP with or without sBAT. In treatment study, the present inventors infused volume (10 ml/kg) and worsened AHF by elevating LVEDP. The present inventors compared major hemodynamic responses before (Baseline) and after sBAT.

Figure 8:
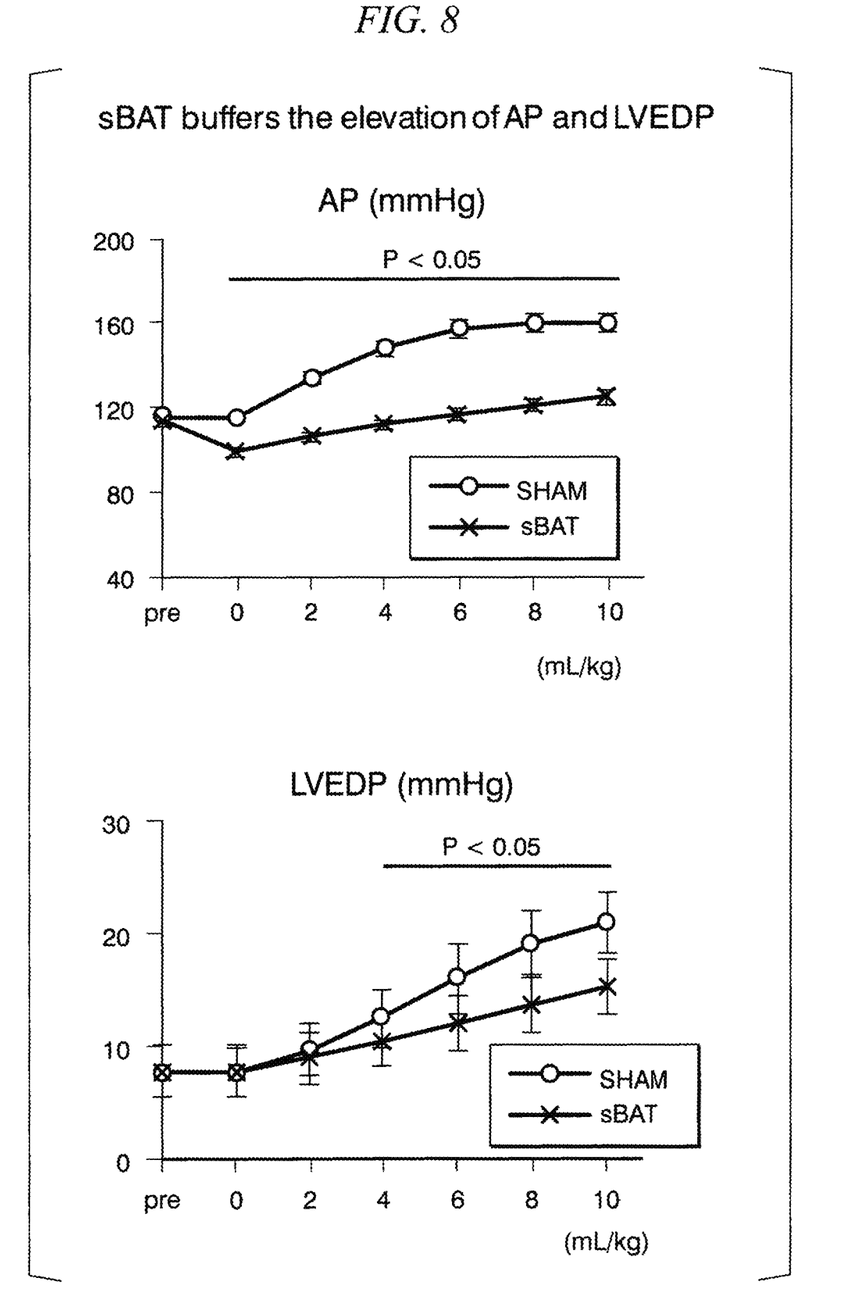
FIG. 8 shows the sBAT suppressing AP and LVEDP in response to volume change.
Figure 9:
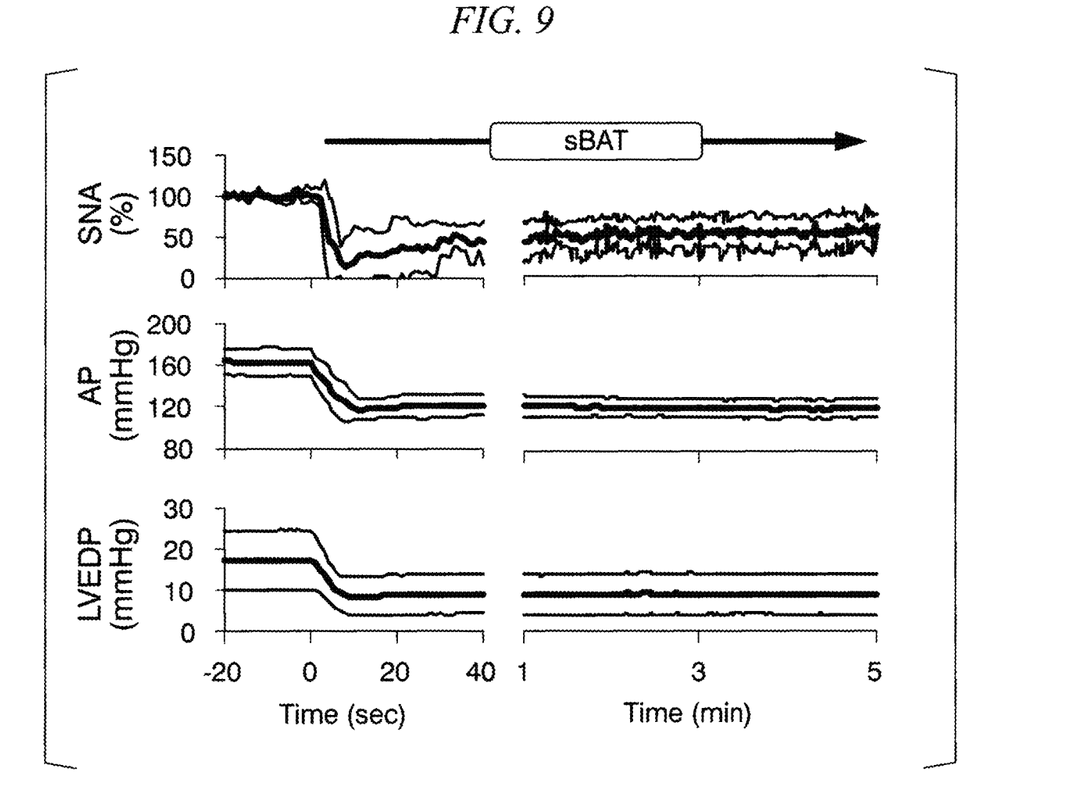
FIG. 9 shows the sBAT instantly improving hemodynamics in AHF.

In volume tolerance study, sBAT nearly halved ($p<0.05$) changes in AP and LVEDP (see FIG. 8) indicating marked improvement of volume tolerance. In treatment study, sBAT instantly and strikingly suppressed LVEDP (Baseline: 20.5±5.1, sBAT 10.8±4.8 mmHg, $p<0.05$) and AP (Baseline: 165.3±14.0, sBAT 119.7±8.8 mmHg, $p<0.05$), without causing excessive hypotension. The rise time (80% of maximum steady state value) of LVEDP was extremely brief (5.2±1.2 sec, see FIG. 9).

sBAT markedly improves volume tolerance and instantly resolves pulmonary congestion in AHF model rats. sBAT may serve as a new therapeutic strategy for AHF.

The present inventors have developed sBAT not only to reconstruct physiological functions but also outperforms the native baroreflex function.

AHF increases SNA which, in turn, increases pre- and after-load and frequently leads to hypertension with life threatening pulmonary edema. Thus, sympathetic unloading is a reasonable therapeutic option.

Baroreflex failure deteriorates volume tolerance, and increases the risk of pulmonary congestion.

The present inventors hypothesized that in AHF with baroreflex failure, sBAT suppresses SNA and resolves pulmonary congestion.

To examine if sBAT suppresses SNA and resolves pulmonary congestion in AHF rats with baroreflex failure.
Animals: Sprague Dawley Rats (BW 370-402 g, N=8)
Anesthesia: Mixture of urethane and α-chloralose
LV dysfunction: LAD ligation The present inventors infused saline stepwise up to 10 mL/kg in 6 min, measured AP, LVEDP and SNA, and compared those between sBAT and control.

The present inventors induced AHF by acute volume infusion (10 mL/kg) and assessed the impact of sBAT on hemodynamics.

sBAT navigated AP to the target pressure (120 mmHg).

sBAT markedly and instantly reduced LVEDP by 8.1±2.9 mmHg. The settling time (80% of maximum response) was extremely brief (5.2±1.2 sec).

AHF of clinical Scenario (CS) 1, which represents the pulmonary edema with high blood pressure, might be a good indication of sBAT.

The development of technology that can servo control SNA and AP will revolutionize the management of AHF.

sBAT markedly improves volume tolerance and instantly (within 5 seconds) resolves pulmonary congestion in AHF model rats. sBAT may serve as a novel therapeutic strategy for AHF via sympathetic unloading.

The various illustrative logical blocks, modules, and algorithm operations described in connection with the embodiments disclosed herein may be implemented as electronic hardware, computer software, or combinations of both. To clearly illustrate this interchangeability of hardware and software, various illustrative components, blocks, modules, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the claims.

The hardware used to implement the various illustrative logics, logical blocks, and modules described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver smart objects, e.g., a combination of a DSP and a microprocessor, two or more microprocessors, one or more microprocessors in conjunction with a DSP core, or any other such configuration. Alternatively, some operations or methods may be performed by circuitry that is specific to a given function.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

REFERENCE SIGNS LIST

1 System
10 Blood pressure controlling apparatus
10A Acquiring part
10B Producing part
10B1 Stimulation frequency calculating part
10B2 Gain adjusting part
10B3 Reference pressure adjusting part
10B4 Initial value setting part
10C Supplying part
11 Detecting part
11A blood pressure sensor
12 Electrode

What is claimed is:

1. A blood pressure controlling apparatus comprising a computer configured to execute a program to:
   acquire biological information indicating blood pressure of a subject;
   produce a frequency modulated pulse train on the basis of the biological information;
   supply an electrical current on the basis of the frequency modulated pulse train to an electrode attached on the subject, wherein the electrical current stimulates baroreceptor afferent nerves of the subject;
   adjust a value of the gain; and
   increase the value of the gain when the variability of the blood pressure is larger than a predetermined value.

2. The blood pressure controlling apparatus according to claim 1 further configured to execute the program to:
   calculate a stimulation frequency of the frequency modulated pulse train on the basis of a gain, a reference pressure, and the blood pressure indicated by the biological information.

3. The blood pressure controlling apparatus according to claim 2 further configured to execute the program to:
   calculate the stimulation frequency by multiplying a difference between the reference pressure and the blood pressure by the gain.

4. The blood pressure controlling apparatus according to claim 1 further configured to execute the program to:
   adjust a value of the reference pressure.

5. The blood pressure controlling apparatus according to claim 4 further configured to execute the program to:
   set an initial value of the gain and an initial value of the reference pressure.

6. The blood pressure controlling apparatus according to claim 5 further configured to execute the program to:
   adjusts the value of the gain on the basis of variability of the blood pressure indicated by the biological information.

7. The blood pressure controlling apparatus according to claim 1 further configured to execute the program to:
   produce the frequency modulated pulse train on the basis of a closed-loop negative feedback system which operates in parallel with a native baroreflex system to augment a native baroreflex function.

8. The blood pressure controlling apparatus according to claim 1 further configured to execute the program to:
   produce the frequency modulated pulse train on the basis of the biological information to control a mean of the blood pressure and to attenuate variability of the blood pressure, independently.

9. The blood pressure controlling apparatus according to claim 5 further configured to execute the program to:
   set the initial value of the reference pressure on the basis of therapeutic requirements or physiological blood pressure change in the subject.

10. The blood pressure controlling apparatus according to claim 1 further configured to execute the program to:
    produce the frequency modulated pulse train on the basis of instantaneous blood pressure indicated by the biological information.

11. The blood pressure controlling apparatus according to claim 10 further configured to execute the program to:
    produce the frequency modulated pulse train on the basis of the instantaneous blood pressure indicated by the biological information by making use of limited baroreflex speed of physiological systems.

12. The blood pressure controlling apparatus according to claim 2, wherein the gain is physiologically frequency dependent.

13. The blood pressure controlling apparatus according to claim 2, wherein the gain is frequency dependent to suppress the blood pressure and variability of the blood pressure frequency dependently.

14. The blood pressure controlling apparatus according to claim 2, wherein the gain is calibrated according to the subject.

15. The blood pressure controlling apparatus according to claim 2, wherein the gain is quantitatively adjusted to make a mean of the blood pressure and variability of the blood pressure programmable.

16. The blood pressure controlling apparatus according to claim 1, wherein the blood pressure controlling apparatus is applied to a controlling system for independently controlling a mean of the blood pressure and variability of the blood pressure.

17. The blood pressure controlling apparatus according to claim 1, wherein the blood pressure controlling apparatus is applied to a system for improving volume tolerance and resolving pulmonary congestion in acute heart failure.

18. A non-transitory computer readable recording medium storing a control program of a blood pressure controlling apparatus, the control program making the blood pressure controlling apparatus perform at least:
    acquiring biological information indicating blood pressure of a subject;
    producing a frequency modulated pulse train on the basis of the biological information; and
    supplying an electrical current on the basis of the frequency modulated pulse train, to an electrode attached on the subject, wherein the electrical current stimulates baroreceptor afferent nerves of the subject; wherein:
    the producing includes a gain adjusting configured to adjust a value of the gain; and
    the gain adjusting increases the value of the gain when the variability of the blood pressure is larger than a predetermined value.

19. A method for controlling blood pressure, the method comprising:
    acquiring biological information indicating blood pressure of a subject;
    producing a frequency modulated pulse train on the basis of the biological information; and
    supplying an electrical current on the basis of the frequency modulated pulse train, to an electrode attached on the subject, wherein the electrical current stimulates baroreceptor afferent nerves of the subject; wherein:
    the producing includes a gain adjusting configured to adjust a value of the gain; and
    the gain adjusting increases the value of the gain when the variability of the blood pressure is larger than a predetermined value.

* * * * *